United States Patent
Brown et al.

(10) Patent No.: US 11,931,394 B2
(45) Date of Patent: *Mar. 19, 2024

(54) HERBAL SUPPLEMENTS AND METHODS OF USE THEREOF

(71) Applicant: KBS Research, LLC, Dallas, TX (US)

(72) Inventors: Kenneth Brown, Plano, TX (US); Brandi M. Scott, Rowlett, TX (US)

(73) Assignee: KBS RESEARCH, LLC, Dallas, TX (US)

( * ) Notice: Subject to any disclaimer, the term of this patent is extended or adjusted under 35 U.S.C. 154(b) by 237 days.

This patent is subject to a terminal disclaimer.

(21) Appl. No.: 17/168,483

(22) Filed: Feb. 5, 2021

(65) Prior Publication Data
US 2021/0154257 A1    May 27, 2021

Related U.S. Application Data

(63) Continuation of application No. 16/010,217, filed on Jun. 15, 2018, now Pat. No. 10,940,176, which is a continuation of application No. 14/978,883, filed on Dec. 22, 2015, now Pat. No. 10,022,413, which is a continuation of application No. 14/072,502, filed on Nov. 5, 2013, now Pat. No. 9,248,158.

(60) Provisional application No. 61/728,893, filed on Nov. 21, 2012.

(51) Int. Cl.
| *A61K 36/77* | (2006.01) |
| *A61K 9/00* | (2006.01) |
| *A61K 36/22* | (2006.01) |
| *A61K 36/24* | (2006.01) |
| *A61K 36/534* | (2006.01) |

(52) U.S. Cl.
CPC ............ *A61K 36/77* (2013.01); *A61K 9/0053* (2013.01); *A61K 36/22* (2013.01); *A61K 36/24* (2013.01); *A61K 36/534* (2013.01)

(58) Field of Classification Search
None
See application file for complete search history.

(56) References Cited

U.S. PATENT DOCUMENTS

| 2007/0249543 A1 | 10/2007 | Zadini et al. |
| 2007/0254050 A1 | 11/2007 | Quart et al. |
| 2008/0220101 A1 | 9/2008 | Buchwald-Werner |
| 2008/0268024 A1 | 10/2008 | Prous et al. |
| 2010/0008887 A1 | 1/2010 | Nakamoto et al. |

FOREIGN PATENT DOCUMENTS

| CN | 101023952 | 8/2007 |
| FR | 2770228 | 4/1999 |
| WO | 2007130892 | 11/2007 |
| WO | 2012131728 | 10/2012 |

OTHER PUBLICATIONS

U.S. Appl. No. 14/072,502, filed Nov. 5, 2013, Patented.
U.S. Appl. No. 14/978,883, filed Dec. 22, 2015, Patented.
U.S. Appl. No. 16/010,217, filed Jun. 15, 2018, Pending.
Becker, K., et al. "Effects of dietary tannic acid and quebracho tannin on growth performance and metabolic rates of common carp (*Cyprinus carpio* L.)", Aquaculture, May 15, 1999, vol. 175, Issues 3-4, pp. 327-335.
Durmic, Z., et al. "Bioactive plants and plant products: Effects on animal function, health and welfare", Animal Feed Science and Technology, Sep. 21, 2012, vol. 176, Issues 1-4, pp. 150-162.
Zotte, A.D. et al., "Dietary inclusion of tannin extract from red quebracho trees (*Schinopsis* spp.) in the rabbit meat production", Italian Journal of Animal Science, vol. 8(2), 2009, pp. 784-786.
Cappello, G. et al., "Peppermint oil (Mintoil) in the treatment of irritable bowel syndrome: a prospective double blind placebo-controlled randomized trial", Digestive and Liver Disease, 2007, vol. 39(6), pp. 530-536.
Cappello, G. et al., "Peppermint oil (Mintoil) in the treatment of irritable bowel syndrome: a prospective double blind placebo-controlled randomized trial", Gastroenterology, 2006, vol. 130(29), Suppl. 2, M1197, pp. A322-A323.
Min, B.R. et.al., "Effects of condensed tannins supplementation level on weight gain and in vitro and in vivo bloat precursors in steers grazing winter wheat", Journal of Animal Science, 2006, vol. 84, No. 9, pp. 2546-2554.
Fu, F. et. al., "Escin: Inhibiting Inflammation and Promoting Gastrointestinal Transit to Attenuate Formation of Postoperative Adhesions", World Journal of Surgery, 2005, vol. 29, No. 12, pp. 1614-1620.
Grigoleit, H.G. et. al., "Peppermint oil in irritable bowel syndrome", Phytomedicine, 2005, vol. 12, No. 8, pp. 601-606.
File history of U.S. Appl. No. 16/010,217, filed Jun. 15, 2018.
File history of U.S. Appl. No. 14/978,883, filed Dec. 22, 2015.
File history of U.S. Appl. No. 14/072,502, filed Nov. 5, 2013.

*Primary Examiner* — Terry A Mckelvey
*Assistant Examiner* — Catheryne Chen
(74) *Attorney, Agent, or Firm* — Ping Wang; Rimon Law

(57) ABSTRACT

In one embodiment, the present application provides an herbal supplement and method for treating bloating, constipation and/or weight gain in a human subject comprising orally administering to a subject in need thereof an effective amount of the herbal supplement comprising a red quebracho extract. In other embodiments, the supplement may additionally include a triterpenoid saponin, an anti-spasmodic agent, or both.

19 Claims, No Drawings

HERBAL SUPPLEMENTS AND METHODS OF USE THEREOF

This application is a Continuation of U.S. application Ser. No. 16/010,217, filed Jun. 15, 2018, which is Continuation of U.S. application Ser. No. 14/978,883, filed Dec. 22, 2015, now U.S. Pat. No. 10,022,413, which is a Continuation of U.S. application Ser. No. 14/072,502, filed Nov. 5, 2013, now U.S. Pat. No. 9,248,158, which claims priority to U.S. Provisional Patent Application No. 61/728,893, filed Nov. 21, 2012. The entirety of the aforementioned application is incorporated herein by reference.

FIELD

The present application relates to herbal compositions and methods for treating diseases associated with bloating, constipation and/or weight gain. More particularly, the present application relates to an herbal supplement and method comprising oral administration of condensed tannins in human subjects for treating bloating, constipation and/or weight gain.

BACKGROUND

Bowel disorders are often characterized by bloating and constipation and are thought to affect at least 20% of the population. Yet, to date no effective therapy is available. Such bowel disorders include irritable bowel syndrome (IBS), functional constipation, chronic pseudo-obstruction, and chronic abdominal bloating syndrome. Symptoms include abdominal pain, constipation, bloating, acid reflux, flatulence, nausea and vomiting, chronic lethargy and sleep disorders.

IBS is a gastrointestinal disorder characterized by chronic abdominal pain and altered bowel habits with either constipation (IBS-C), diarrhea (IBS-D) or both (IBS-M; mixed type). IBS is the most commonly diagnosed GI condition. It is second only to the common cold as a cause of absence from work. It is estimated that around 20% of the general population suffers from IBS, resulting in increased health care costs. Annual direct and indirect costs are reported to be of up to $30 billion.

Functional constipation is the most common gastrointestinal complaint affecting the 63 million Americans with IBS. IBS is often characterized by hard stools or straining or having fewer than 3 bowel movements a week at least 25 percent of the time.

Despite the seriousness of IBS as a health care issue the underlying causes remain largely unknown. The traditional focus has been on alterations in the GI motility and on visceral hypersensitivity. Recent reports suggest that small intestinal bacterial overgrowth (SIBO) may play a significant role in the development of IBS, as well as obesity and type II diabetes. For example, multiple studies have demonstrated excessive coliform bacteria in the small intestines of IBS patients.

Methanogenic archaebacteria are an important group of gut colonizing bacteria contributing to SIBO that grow primarily under anaerobic conditions and produce methane ($CH_4$) as a by-product of fermentation. The degradation of carbohydrates by enteric bacteria, including methanogenic bacteria, leads to the production of short chain fatty acids (butyrate, propionate, acetate), as well as carbon dioxide, hydrogen and methane. These products are associated with acidic stools, abdominal distension, flatulence, diarrhea, and constipation. Methanogenic bacteria are unique, in that their metabolism increases in the presence of products from other bacteria. They use hydrogen and ammonia from other bacteria as substrates for the production of methane. Intestinal methane production has been linked to IBS-C, functional constipation, obesity and type II diabetes. The methane directly influences the colonic transit time, colonic motility, and rectal sensorimotor function resulting in lowered pain threshold.

There is growing evidence that the microbiota plays a critical role in the determinant of nutrient uptake, energy regulation and ultimately weight and metabolic disorders. Gut microbes can influence both the harvest of energy from components of the diet and how energy is stored and expended. In this regard, methane-producing bacteria have been found to be present in greater abundance in obese mice and humans compared with lean animals and individuals. It has been shown that hydrogen transfer between bacterial and archaeal species may increase energy uptake by the large intestine via methanogens by removing fermentation intermediates, such as $H_2$ or formate. This allows greater production and availability of short chain fatty acids for absorption across the intestinal lumen. The methane produced also acts as a local paralytic allowing food substrates to have longer contact with the absorptive villi in the small bowel.

Treatment options for gastrointestinal disorders and obesity are limited. For example, although there are treatment options for IBS including the use of bulking agents, such as fiber, antispasmodics, antidepressants, and more recently probiotics and antibiotics, such treatment options are not sufficiently effective and do not treat the underlying problem. For example, bulking agents have not been shown to demonstrate an improvement in global IBS symptoms and actually have been shown to increase bloating and pain. Anti-spasmodics available in the US for IBS include dicyclomine, hyoscyamine, and peppermint oil. A recent meta-analysis found only peppermint oil to be effective in improving global IBS symptoms. Antidepressants have shown poor and conflicting results, ultimately demonstrating no relief in symptoms. Regarding probiotics, a large meta-analysis demonstrated no superior effect over placebo. And, of course, obesity is an epidemic problem with few effective options.

Surveys have demonstrated that less than 14% of patients with IBS are satisfied with their treatment. Presently, there are few dependable pharmaceutical treatment options for IBS or obesity.

In view of the current shortcomings associated with bowel disorder treatments, including IBS and functional constipation, as well as obesity or undesired weight gain, there is a need for new treatments. The present application addresses this need and provides new methods and formulations for treating such disorders or diseases.

SUMMARY

The present application relates to herbal compositions and methods for treating diseases associated with bloating, constipation and/or weight gain. In one aspect, the present application provides a method for treating bloating, constipation or weight gain comprising orally administering to a human subject in need thereof an herbal supplement comprising condensed tannins in an amount effective to reduce bloating, constipation and/or weight gain.

In some embodiments, the method employs an herbal supplement comprising a red quebracho extract. In other embodiments, the supplement additionally includes either an herbal composition comprising a triterpenoid saponin, an herbal composition comprising an anti-spasmodic agent, or both.

The compositions and methods may be applied to treating bowel disorders characterized by bloating or constipation, as well as obesity and other conditions characterized by undesirable weight gain. Exemplary bowel disorders for treatment include irritable bowel syndrome (IBS), functional constipation and chronic abdominal bloating syndrome. The compositions may be further applied to managing or controlling obesity or type II diabetes.

In one embodiment, the herbal supplement comprises a red quebracho extract and an herbal supplement comprising either a triterpenoid saponin, an anti-spasmodic agent, or both, wherein the supplement is formulated to reduce bloating, constipation, and/or weight gain. In another embodiment, the herbal supplement comprises a red quebracho extract and a nutraceutically acceptable carrier, wherein the supplement is in the form of a tablet or capsule.

The red quebracho extract may be derived from any red quebracho tree. Exemplary red quebracho species include *Shinopsis lorentzii, Schinopsis balansae, Schinopsis brasiliensis, Schinopsis haenkeana, Schinopsis heterophylla* and *Schinopsis marginata*. Preferably, the supplement comprises red quebracho extract having a condensed tannin content between about 50% and about 80%. Condensed tannins are known to bind, precipitate and/or shrink proteins, and to negatively impact the activity of protozoa and methanogenic bacteria.

In certain embodiments, the triterpenoid saponin is provided in the form of a plant extract, such as an *Aesculus* or *Satindus* species plant extract. In plants, triterpenoid saponins are considered defensive compounds against pathogenic microbes and herbivores. Triterpenoid saponins are useful in view of their antibacterial properties, including an ability to counteract bacteria and fungi though cell surface interactions therewith and in their ability to complex with carbohydrates to improve digestibility. In one embodiment, the triterpenoid saponin is provided in the form of a horse chestnut (*Aesculus hippocastanum*) extract, soapnut (*Satindus trifoliatus*) extract, or seed extract thereof.

In some embodiments, the herbal supplement includes one or more anti-spasmodic agents in the form of an herbal extract derived from a plant. Anti-spasmodic (or spasmolytic) agents prevent or ease spasms or cramps in muscles, and provide particular benefit in the muscles of the gut and bladder of IBS patients, especially in regard to reducing abdominal pain, calming and soothing the digestive system and relaxing the gastro-esophageal sphincter. Exemplary anti-spasmodic agent sources include plants, such as barberry, basil, black cohosh, centella, chamomile, cramp bark, dill, fennel, ginger, hawthorn, hops, juniper berries, lemon balm, licorice, marshmallow, nutmeg, peppermint, rosemary, saffron, sage, skullcap, slippery elm, spearmint, thyme, valerian, wild lettuce and wild yam. In one embodiment, the anti-spasmodic agent is provided in the form of a peppermint oil.

In a particular embodiment, the herbal supplement is in a dosage form that comprises between about 20 to 500 mg of red quebracho extract; between about 100 to about 2000 mg of *Aesculus hippocastanum* plant extract; and between about 0.05 to about 1 ml of peppermint oil.

DETAILED DESCRIPTION

The following detailed description is presented to enable any person skilled in the art to make and use the present application. For purposes of explanation, specific nomenclature is set forth to provide a thorough understanding of the present application. However, it will be apparent to one skilled in the art that these specific details are not required to practice the present application. Descriptions of specific applications are provided only as representative examples. The present application is not intended to be limited to the embodiments shown, but is to be accorded the widest possible scope consistent with the principles and features disclosed herein.

Unless otherwise defined, scientific and technical terms used in connection with the present application shall have the meanings that are commonly understood by those of ordinary skill in the art. Further, unless otherwise required by context, singular terms shall include pluralities and plural terms shall include the singular.

DEFINITIONS

As used herein, the following terms shall have the following meanings:

as used herein, the term "herbal composition" is used with reference to any phytochemical or mixture thereof that is obtained, isolated, and/or derived from one or more extracts of plant material(s) or essential oil(s) thereof. The term "plant material" refers to any plant material including, but not limited to, leaves, hark, stems, flowers, fruits, seeds, roots, and combinations thereof. The terms "herbal extract," and "plant extract" are used interchangeably with reference to a plant material directly extracted from a plant. An extract may be in the form of a dry powder, solution or oil.

As used herein, the phrase "treating" or "treatment" of weight gain is synonymous with promotion of weight loss, as well as controlling or managing body weight, or more specifically, prevention of weight gain and/or inhibiting the promotion of weight gain.

The term "nutraceutically acceptable," such as in the recitation of a "nutraceutically acceptable carrier," refers to a material that is not biologically or otherwise undesirable, i.e., the material may be incorporated into a pharmaceutical composition administered to a patient without causing any undesirable biological effects or interacting in a deleterious manner with any of the other components of the composition in which it is contained.

An "effective amount" refers to a nontoxic but sufficient amount of a composition or plant material to provide a desired systemic or local effect. The effective amount will vary with the nature of the composition and constituent parts, the age and physical condition of the end user, the severity of the bowel disorder, the duration of the treatment, the nature of concurrent therapy, the particular pharmaceutically acceptable carrier utilized, and like factors. As used herein, all percentages are by weight unless otherwise specified.

As used herein the transitional term "comprising" and "comprises" are synonymous with "including," "containing," or "characterized by," any one of which is inclusive or open-ended and does not exclude additional, unrecited elements or method steps, regardless of its use in the preamble or the body of a claim. The term further encompasses the terms "consisting of" and "consisting essentially of". In the claims and/or the specification, "comprising" may mean "one," but it is also consistent with the meaning of "one or more," "at least one," and "one or more than one."

The present application relates to herbal compositions and methods for treating bowel disorders associated with bloating, constipation and weight gain. More particularly, the present application relates to an herbal supplement and method comprising oral administration of condensed tannins in human subjects for treating bloating, constipation and/or weight gain. In one embodiment, a method for treating bloating, constipation and/or weight gain comprises orally administering to a human subject in need thereof an herbal supplement comprising condensed tannins in an effective amount, wherein the supplement is formulated to reduce bloating, constipation and/or weight gain.

The compositions and methods apply to any bowel disorder characterized by bloating, constipation, or both, as well as obesity and other diseases characterized by unwanted weight gain. Exemplary bowel disorders for treatment include irritable bowel syndrome (IBS), functional constipation, and chronic abdominal bloating syndrome.

In certain embodiments, the compositions and methods relate to treating one or more symptoms of an IBS disease subtype, including bloating and/or constipation. According to the Rome III classification system, there are four recognized subtypes of IBS: a) constipation-predominant IBS (IBS-C), characterized by hard or lumpy stools in ≥25% of bowel movements and loose (mushy) or watery stools in <25% of bowel movements; b) diarrhea-predominant IBS (IBS-D), characterized by loose (mushy) or water stools in ≥25% of bowel movements and hard or lumpy stools in <25% of bowel movements; and c) mixed-type IBS (IBS-M; sometimes diarrhea, sometimes constipation), characterized by hard or lumpy stools in ≥25% of bowel movements and loose (mushy) or watery stools in ≥25% of bowel movements; and d) unsubtyped IBS (IBS-U), characterized by insufficient abnormality of stool consistency to meet the criteria for IBS-C, D, or M. Alternating IBS (IBS-A) accounts for a large proportion of patients whose bowel habit oscillate from diarrhea to constipation and vice versa, such that up to 75% of patients (or more) transition between IBS-D and IBS-C over a 1 year period.

In one embodiment, the herbal supplement comprises a red quebracho extract and an herbal supplement comprising either a triterpenoid saponin, an anti-spasmodic agent, or both, wherein the supplement is formulated to reduce one or more bowel disorder symptoms in a human subject, including bloating, constipation or both. Additional symptoms treated by compositions of the present application may include pain; abdominal fullness, abdominal distension; abnormal stool frequency, i.e., fewer than three bowel movements per week or more than three bowel movements per day; hard or lumpy stools, sometimes loose (mushy) or watery stools; straining during a bowel movement; urgency (having to rush to have a bowel movement); feeling of incomplete bowel movement; or passing of mucus during a bowel movement.

In a further aspect, the present application provides a method for managing or controlling weight gain, obesity or type II diabetes comprising orally administering to a human subject in need thereof an herbal supplement as described herein, in an amount effective to reduce weight gain or reduce one or more symptoms of obesity or type II diabetes.

The herbal supplement may be prepared using any suitable plant extract(s), preferably at least one known to possess a high condensed tannin content. Condensed tannins are a complex group of polyphenolic compounds found in a wide variety of plant species. Condensed tannins or proanthocyanidins, are non-branched polymers of flavonoid units (e.g., flavan-3-ol, flavan-3,4-diol), and usually have a molecular weight of about 1-20 kDa.

Condensed tannins bind, precipitate and/or shrink proteins and have been shown to reduce methane levels by negatively impacting the activity of protozoa and methanogenic bacteria in the gut. In addition, condensed tannins form complexes with carbohydrates and proteins to improve protein metabolism, improve digestibility and reduce constipation.

The gut microbiota plays an important role in the regulation of energy and weight control and is believed to influence the development and progression of obesity and type 2 diabetes. Accordingly, the gut microbiome further represents a target for condensed tannins, not only in the treatment of the above-described bowel disorder, but in the treatment of obesity and/or type II diabetes as well.

Plant parts containing tannins include bark, wood, fruit, fruitpods, leaves, roots and plant galls. Condensed tannins may be provided in the form of plant extracts derived from selected plants (and their representative members), including but not limited to birch (*Betula* sp.), canaigre (*Rumex hymenocephalus*), chestnut wood (*Castanea* sp., incl. *sativa* and *dentata*), Eastern hemlock (*Tsuga canadensis*), eucalyptus (*Eucalyptus* sp.), European larch (*Latrix decidua*), mangrove (*Rhizophora* sp., incl. *mangle*), oak (*Quercus* sp., incl. *montana*), pine (*Pinus* sp.), pomegranate (*Punica granatum*), red quebracho (*Schniposis* sp.), rhatany root (*Krameria triandra*), Scotch pine bark (*Pinus sylvestris*), spruce (*Picea* sp., incl. *abies*), sumac (*Rhus* sp.), wattle (*Acacia* sp., incl. *decurrens* and *mearnsii*), willow (*Salix caprea*) and wine grape seed (*Vitis vinifera*).

In a preferred embodiment, the method employs an herbal supplement in which a red quebracho extract provides the condensed tannins. The red quebracho extract may be derived from any red quebracho tree, including but not limited to *Shinopsis lorentzii, Schinopsis balansae, Schinopsis brasiliensis, Schinopsis haenkeana, Schinopsis heterophylla* and *Schinopsis marginata*. In one embodiment, the red quebracho extract is prepared from the bark of a red quebracho tree.

In the present application, red quebracho extracts may comprise at least 25%, at least 40%, at least 50%, at least 60%, at least 70%, at least 80% or at least 90% or more condensed tannins (w/w). In one embodiment, the red quebracho extract is substantially free of hydrolyzable tannins. Alternatively, or in addition, the red quebracho extract is in the form of a powder. In one embodiment, the red quebracho extract is in the form of a powder with a condensed tannin content of at least 80%. When administered in a capsule, the red quebracho extract preferably comprises a powder, substantially free of hydrolysable tannins and having a condensed tannin content of at 50%, at least 60%, at least 70% or about 73%.

The red quebracho extract may be present in any amount sufficient for treating bloating or constipation. In some embodiments, the herbal supplement is in a dosage form that comprises red quebracho extract in an amount between about 10 to about 1000 mg, between about 25 to about 500 mg, or between about 50 to about 200 mg.

In other embodiments, the herbal supplement additionally includes either an herbal composition comprising a triterpenoid saponin, an herbal composition comprising an anti-spasmodic agent, or both, wherein the supplement is formulated to reduce one or more symptoms of a bowel disorder in a human subject characterized by bloating or constipation. In another embodiment, the herbal supplement comprises a red quebracho extract and a nutraceutically acceptable carrier, wherein the supplement is in the form of a tablet or capsule.

Triterpenoid saponins belong to a large group of structurally diverse surface-active glycoside compounds that are found in a wide variety of plant species. Triterpenoid saponin compounds typically contain sugars moieties in a four or five ring configuration of about 30 carbons with several oxygens attached. In plants, triterpenoid saponins are considered defensive compounds against pathogenic microbes and herbivores. Triterpenoid saponins are useful in the treatment of bloating, constipation and/or weight gain in view of their antibacterial properties, including an ability to counteract bacteria and fungi though cell surface interactions therewith and in their ability to complex with carbohydrates to improve digestibility.

In certain embodiments, the triterpenoid saponin is provided in the form of a plant extract, such as an *Aesculus* or *Sapindus* species plant extract. In certain particular embodiments, the triterpenoid saponin is provided in the form of a horse chestnut (*Aesculus hippocastanum*) extract or a soapnut (*Satindus trifoliatus*) extract, including seed extracts thereof.

Anti-spasmodic (or spasmolytic) agents prevent or ease spasms or cramps in muscles, and provide particular benefit in the muscles of the gut and bladder of IBS patients, especially with regard to their ability to reduce abdominal pain, calm and sooth the digestive system, relax gastrointestinal smooth muscles, relax the gastro-esophageal sphincter and to increase time and absorption of therapeutic agents into the small intestine. A wide variety of plants are known to naturally synthesize anti-spasmodic agents.

In some embodiments, the anti-spasmodic agent is provided in the form of an herbal extract derived from selected plants (and their representative members), including but not limited to barberry (*Berberis vulgaris*), basil (*Ocimum basilicum*), black cohosh (*Actaea racemosa*), centella (*Centella asiatica*), chamomile (*Matricaria recutita*), cramp bark (*Viburnum opulus*), dill (*Anethum graveolens*), fennel (*Foeniculum vulgare*), ginger (*Zingiber officinale*), hawthorn (*Crataegus monogyna*), hops (*Humulus lupulus*), juniper berries (*Juniperus communis*), lemon balm (*Melissa officinalis*), licorice (*Glycyrrhiza glabra*), marshmallow (*Althaea officinalis*), nutmeg (*Myristica fragrans*), peppermint (*Mentha piperita*), rosemary (*Rosmarinus offinalis*), saffron (*Crocus sativus*), sage (*Salvia officinalis*), skullcap, (*Scutellaria baicalensis*), slippery elm (*Ulmus rubra*), spearmint (*Mentha spicata*), thyme (*Thymus vulgaris*), valerian (*Valeriana officinale*), wild lettuce (*Lactuca virosa*) and wild yam (*Dioscorea villosa*).

In a particular embodiment, the anti-spasmodic agent is provided in the form of peppermint oil, a well know flavoring agent derived from the leaves and flowering tops of the *Mentha piperita* L plant, a hybrid mint that is a cross between watermint and spearmint.

When used alone, the red quebracho extract may be present in the herbal supplement in an amount between about 1% to about 100% by weight of the total supplement. When used in conjunction with other herbal compositions described herein, the quebracho extract may be present in the herbal supplement in an amount between about 0.5% to about 75%, between about 2% to about 40%, or between about 5% to about 20% by weight of the total supplement.

When the herbal composition comprising the triterpenoid saponin is provided in the form of an herbal extract, the extract may be present in the herbal supplement in an amount between about 10% to about 90%, between about 20% to 80%, or between about 40% and about 65% by weight of the herbal supplement. In some embodiments, the herbal supplement is in a dosage from that comprises a triterpenoid saponin in an amount between about 50 to about 2000 mg, between about 150 to about 1000 mg, or between about 300 to 600 mg.

When the herbal composition comprising the anti-spasmodic agent is provided in the form of an extract, the extract may be provided in an amount between about 2% to about 70%, more preferably between about 5% to 40%, more preferably between about 15% to about 30% by weight of the herbal supplement. In some embodiments, the herbal composition is in a dosage form that comprises the anti-spasmodic agent in an amount between about 10 to about 1000 mg, between about 50 to about 500 mg or between about 100 to about 300 mg.

The herbal supplement may comprises one or more extracts separately administered in combination with one another (e.g. in the form of capsules or tablets) or they may be administered together in a single formulation comprising a red quebracho extract, a triterpenoid saponin and an anti-spasmodic agent.

In one embodiment, the herbal supplement is in a dosage form that comprises between about 20 to 500 mg of red quebracho extract; between about 100 to about 2000 mg of *Aesculus hippocastanum* plant extract; and between about 0.05 to about 1 ml of peppermint oil. In a particular embodiment, the herbal supplement comprises 100 mg red quebracho extract, 470 mg *Aesculus hippocastanum* extract and 180 mg peppermint oil.

Extracts for use in the present application may be produced from any plant tissues that can be extracted by water, polar, or petroleum solvents for treating irritable bowel syndrome. An extract may be prepared using extraction procedures well known in the art (e.g., the use of organic solvents such as lower alcohols, alkyl esters, alkyl ethers, alkyl ketones, chloroform, petroleum ether, hexane and/or inorganic solvents such as water). Additionally, the extracts may be produced by cold extraction techniques using a variety of different extraction solvents including, but not limited to, water, fatty solvents (such as olive oil), and alcoholic solvents (e.g. 70% ethanol). Cold extraction techniques may be applied to softer parts of the plant such as leaves and flowers, or in cases wherein the desired active components of the plant are heat labile. Alternatively, the aforementioned solvents may be used to produce extracts of the desired plants by a hot extraction technique, wherein said solvents are heated to a high temperature, the precise value of said temperature being dependent on the properties of the chosen solvent, and maintained at that temperature throughout the extraction process. Hot extraction techniques are more commonly applied to the harder, tougher parts of the plant, such as bark, woody branches and larger roots. In some cases, sequential extractions may be performed in more than one solvent, and at different temperatures.

Standard procedures for producing plant extracts (including hot extraction, cold extraction and other techniques) are described in many publications including "Medicinal plants: a field guide to the medicinal plants of the Land of Israel (in Hebrew), author: N. Krispil, Har Gilo, Israel, 1986" and "Making plant medicine, author: R. Cech, pub. by Horizon Herbs, 2000." which are incorporated herein by reference in their entirety. Preferably, the supplement comprises one or more plant extract(s) prepared in powdered form.

Compositions and medicaments containing mixtures of extracts from different plant species, such as those of the present application may be prepared using different ratios of each extract.

In certain embodiments, the supplement may include an herbal extract in the form of an essential oil. As used herein, the term "essential oil" refers to an oil derived from herbs or other plants through steam distillation or cold pressing. An essential oil may be mixed with a vegetable oil or water and may be orally ingested for use in accordance with the present disclosures.

In some cases, leaves from a given plant species may be steam distilled to make the essential oil from that plant species. The essential oil made from a defined tree species may be used interchangeably for the name of the plant species and for the name of the essential oil produced from the leaves and other components of the plant species. Likewise, the same applies to an extract derived from a given plant species.

The herbal supplement can be provided in any nutraceutically acceptable form. Preferably, the herbal supplement is formulated for oral administration as, for example but not limited to, drug powders, crystals, granules, small particles (which include particles sized on the order of micrometers, such as microspheres and microcapsules), particles (which include particles sized on the order of millimeters), beads, microbeads, pellets, pills, microtablets, compressed tablets or tablet triturates, molded tablets or tablet triturates, and in capsules, which are either hard or soft and contain the composition as a powder, particle, bead, solution or suspension.

The herbal supplement can also be formulated for oral administration as a solution or suspension in an aqueous liquid, as a liquid incorporated into a gel capsule or as any other convenient formulation for administration, or for rectal administration, as a suppository, enema or other convenient form. In addition, the compositions of the application can also be provided as a controlled release system.

The herbal supplement may further include any nutraceutically acceptable excipient, carrier or mixture thereof. As used herein, the term "nutraceutically acceptable excipient or carrier" refers to a non-toxic, inert solid, semi-solid, diluent, encapsulating material or formulation auxiliary of any type. Exemplary excipients include, but are not limited to diluents or fillers, such as dextrates, dicalcium phosphate, calcium sulfate, lactose, cellulose, kaolin, mannitol, sodium chloride, dry starch, sorbitol, sucrose, inositol, powdered sugar, bentonite, microcrystalline cellulose, or hydroxypropylmethylcellulose may be added to the inhibitor molecule to increase the bulk of the composition. Also, binders, such as but not limited to, starch, gelatin, sucrose, glucose, dextrose, molasses, lactose, acacia gum, sodium alginate, extract of Irish moss, panwar gum, ghatti gum, mucilage of isapgol husks, carboxymethylcellulose, methylcellulose, polyvinylpyrrolidone, Veegum and starch arabogalactan, polyethylene glycol, ethylcellulose, and waxes, may be added to the supplement to increase its cohesive qualities. Additionally, lubricants, such as but not limited to, talc, magnesium stearate, calcium stearate, stearic acid, hydrogenated vegetable oils, polyethylene glycol, sodium benzoate, sodium acetate, sodium chloride, leucine, carbowax, sodium lauryl sulfate, and magnesium lauryl sulfate may be added to the supplement. Also, glidants, such as but not limited to, colloidal silicon dioxide or talc may be added to improve the flow characteristics of a powdered supplement. Finally, disintegrants, such as but not limited to, starches, clays, celluloses, algins, gums, crosslinked polymers (e.g., croscarmelose, crospovidone, and sodium starch glycolate), Veegum, methylcellulose, agar, bentonite, cellulose and wood products, natural sponge, cation-exchange resins, alginic acid, guar gum, citrus pulp, carboxymethylcellulose, or sodium lauryl sulfate with starch may also be added to facilitate disintegration of the supplement in the intestine.

In certain embodiments, one or more compositions of the supplement may be formulated to protect the composition from degradation by the acidic conditions of the stomach and from interactions with proteins, such as pepsin, present in the stomach. Such a formulation may include a pH-dependent enteric coating to prevent release until after gastric emptying. Thus, in some embodiments, one or more compositions or the entire supplement is enteric coated. However, in other embodiments no compositions of the supplement are enteric coated.

An enteric coated composition or supplement may be formulated as enteric coated tablets, beads or granules, which may optionally contain a lubricant such as, but not limited to, magnesium stearate.

The enteric coating may include one or more pH dependent polymers. The pH dependent polymers may remain intact at pH values lower than about 4.0 and dissolve at pH values higher than 4.0, preferably higher than 5.0, most preferably about 6.0. Exemplary pH-dependent polymers include, but are not limited to, methacarylic acid copolymers, methacrylic acid-methyl methacrylate copolymers (e.g., EUIDRAGIT® L100 (Type A), EUIDRAGIT® S100 (Type B), Rohm GmbH, Germany; methacrylic acid-ethyl acrylate copolymers (e.g., EUDRAGIT® L100-55 (Type C) and EUIDRAGIT® L30D-55 copolymer dispersion, Rohm GmbH, Germany); copolymers of methacrylic acid-methyl methacrylate and methyl methacrylate (EUIDRAGIT® FS); terpolymers of methacrylic acid, methacrylate, and ethyl acrylate; cellulose acetate phthalates (CAP); hydroxypropyl methylcellulose phthalate (HPMCP) (e.g., HP-55, HP-50, HP-55S, Shinetsu Chemical, Japan); polyvinyl acetate phthalates (PVAP) (e.g., COATERIC®, OPADRY® enteric white OY-P-7171); polyvinylbutyrate acetate; cellulose acetate succinates (CAS); hydroxypropyl methylcellulose acetate succinate (HPMCAS), e.g., HPMCAS LF Grade, MF Grade, HF Grade, including AQOAT® LF and AQOAT® MF (Shin-Etsu Chemical, Japan); Shinetsu Chemical, Japan); shellac (e.g., MARCOAT™ 125 & MARCOAT™ 125N); vinyl acetate-maleic anhydride copolymer; styrene-maleic monoester copolymer; carboxymethyl ethylcellulose (CMEC, Freund Corporation, Japan); cellulose acetate phthalates (CAP) (e.g., AQUATERIC®); cellulose acetate trimellitates (CAT); and mixtures of two or more thereof at weight ratios between about 2:1 to about 5:1, such as, for instance, a mixture of EUDRAGIT® L 100-55 and EUDRAGIT® S 100 at a weight ratio of about 3:1 to about 2:1, or a mixture of EUIDRAGIT® L 30 D-55 and EUDRAGIT® FS at a weight ratio of about 3:1 to about 5:1.

The pH dependent polymers can be incorporated in an amount from about 10% to 90%, preferably from about 20% to 80% and most preferably from about 30% to 70% by weight of the dosage unit or supplement. The polymer(s) can be incorporated into the formulation either prior to or after granulation or they can be added into the supplement either as a dry material, or they can be dispersed or dissolved in an appropriate solvent, and dispersed during granulation.

An enteric coated composition or supplement may include enteric coated beads in a capsule, enteric coated microspheres in a capsule, enteric coated microspheres provided in a suspension or mixed with food, which are particularly convenient for pediatric administration, and enteric coated compressed tablets. The capsule can be a hard-shell gelatin capsule or a cellulose capsule. In particular, the composition or herbal supplement may be formulated as an enteric coated capsule. In certain embodiments, an herbal supplement comprising an anti-spasmodic composition, such as peppermint oil is administered in a tablet form that is backfilled with microcrystalline cellulose. Alternatively, the peppermint oil may be administered without the use of an enteric coating.

In some embodiments, the composition(s) and/or supplements may be directly compressed, with or without any excipients, into a tablet or other herbal supplement having a nutraceutically acceptable hardness and friability. Preferably, the directly compressible herbal supplement can be compressed into tablets having a hardness of greater than 4 kp (kiloponds), preferably a hardness of 8 to 14 kp, more preferably a hardness of 10 to 13 kp. A directly compressible composition can be compressed into a tablet that has a friability of not more than 1% loss in weight, preferably less than 0.8% loss in weight, more preferably less than 0.5% loss in weight.

The present application is further illustrated by the following Example that should not be construed as limiting.

EXAMPLE

A single blinded placebo controlled study includes 20 patients presenting with active bloating and constipation receiving either a placebo IN=[10] or an herbal supplement [N=10] according to the present application. Endpoints include relief of gas and bloating, and evaluation of constipation and weight loss. Safety profiles and weight changes are monitored throughout the trial.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the claimed components and steps in any sequence which is effective to meet the objectives there intended, unless the context specifically indicates the contrary.

What is claimed is:

1. An herbal supplement, comprising:
   (1) a red quebracho extract in an amount between about 0.5% to about 75% by weight the total supplement; and
   (2) an herbal composition comprising a triterpenoid saponin in an amount betweent about 10% to about 90% by weight of the total supplement.

2. The herbal supplement of claim 1, wherein the red quebracho extract comprises condensed tannins in an amount betweent 50% to about 80%.

3. The herbal supplement of claim 1, wherein the triterpenoid saponin is provided in the form of a plant extract.

4. The herbal supplement of claim 1, wherein the triterpenoid saponin is provided in the form of a plant extract in an amount between about 40% and about 65% by weight of the total supplement.

5. The herbal supplement of claim 1, wherein the triterpenoid saponin is provided in the form of an *Aesulus* species plant extract.

6. The supplement of claim 1, wherein the triterpenoid saponin is provided in the form of an *Aesculus hippocustamum* plant extract.

7. The herbal supplement of claim 1, wherein the triterpenoid saponin is provided in the form of an *Satindus* species plant extract.

8. The herbal supplement of claim 1, wherein the triterpenoid saponin is provided in the form of an *Satindus trifoliatus* plant extract.

9. The herbal supplement of claim 1, wherein the herbal supplement is formulated in a dosage form that comprises between about 100 to about 2000 mg of the triterpenoid saponin.

10. The herbal supplement of claim 9, wherein the herbal supplement is formulated in a dosage form that comprises between 300 to about 600 mg of the triterpenoid saponin.

11. An herbal supplement of claim 1, wherein the herbal supplement is formulated in a dosage form that comprises: (1) between about 20 to 500 mg of red quebracho extract; and (2) between about 100 to about 2000 mg of *Aesculus hippocastanum* plant extract.

12. The herbal supplement of claim 1, further comprising a nutraceutically acceptable carrier, wherein the herbal supplement is in the form of a tablet or capsule.

13. A method for reducing bloating in a human subject, comprising: orally administering to a human subject in need thereof an effective amount of the herbal supplmement of claim 1.

14. A method for reducing constipation in a human subject, comprising: orally administering to a human subject in need thereof an effective amount of the herbal supplment of claim 1.

15. A mehtod for reducing weight gain in a human subject, comprising: orally administering to a human subject in need thereof an effective amount of the herbal supplement of claim 1.

16. A method for reducing irritable bowel syndrome in a human subject, comprising: orally administering to a human subject in need thereof an effective amount of the herbal supplmement of claim 1.

17. A method for reducing diarrhea in a human subject, comprising: orally administering to a human subject in need thereof an effective amount of the herbal supplement of claim 1.

18. A method for reducing abdominal discomfort in a human subject, comprising: orally administering to a human subject in need thereof an effective amount of the herbal supplement of claim 1.

19. A method for reducing digestive health in a human subject, comprising: orally administering to a human subject in need thereof an effective amount of the herbal supplmennt of claim 1.

* * * * *